(12) United States Patent
Helland et al.

(10) Patent No.: US 6,671,553 B1
(45) Date of Patent: Dec. 30, 2003

(54) IMPLANTABLE CARDIAC LEAD HAVING TERMINATING CONNECTOR STRAIN RELIEF AND METHOD OF MANUFACTURE

(75) Inventors: John R. Helland, Saugus, CA (US); Phong D. Doan, Stevenson Ranch, CA (US); Yougandh Chitre, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 310 days.

(21) Appl. No.: 09/864,542

(22) Filed: May 23, 2001

(51) Int. Cl.$^7$ .............................................. H61N 1/372
(52) U.S. Cl. ........................................ 607/37; 607/119
(58) Field of Search ................ 439/909; 600/372–374, 600/377; 606/129; 607/37–38, 116, 119, 122, 123, 126

(56) References Cited

U.S. PATENT DOCUMENTS

| | | | |
|---|---|---|---|
| 5,571,145 A | * 11/1996 | Drebin | 607/37 |
| 5,876,430 A | * 3/1999 | Shoberg et al. | 607/122 |
| 5,931,861 A | 8/1999 | Werner et al. | 607/115 |
| 6,038,479 A | 3/2000 | Werner et al. | 607/115 |
| 6,038,481 A | 3/2000 | Werner et al. | 607/119 |

* cited by examiner

*Primary Examiner*—Kennedy Schaetzle
*Assistant Examiner*—Kristen Droesch

(57) ABSTRACT

An implantable cardiac lead includes a connector having strain relief to protect the connector from damage during removal of the connector from an associated implantable cardiac stimulation device. The lead is elongated and has a distal end, a proximal end, an electrode, and a conductor coupled to the electrode and extending to the lead proximal end. A connector on the lead proximal end connects the conductor to a mating implantable device connector. The lead connector includes a body, a terminal carried by the body which is coupled to the conductor, an anchor longitudinally fixed on the lead and to the conductor distal to the terminal, and a strain relief member connected between the anchor and the terminal.

31 Claims, 1 Drawing Sheet

IMPLANTABLE CARDIAC LEAD HAVING TERMINATING CONNECTOR STRAIN RELIEF AND METHOD OF MANUFACTURE

FIELD OF THE INVENTION

The present invention generally relates to an implantable cardiac lead for use with an implantable cardiac stimulation device. The present invention more particularly relates to such a lead and method of making the same wherein the lead includes strain relief to protect the lead connector from damage when the lead connector is withdrawn from an associated device.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are positioned within the heart for making electrical contact with desired heart chambers. Conductors within the leads couple the electrodes to a connector of the lead which in turn is received by a mating connector within a connector receiving cavity of the device. This then couples the electrodes of the lead to the device to enable the device to sense cardiac electrical activity and deliver the desired electrical therapy with the electrodes.

The connection system described above also provides for the leads to be disconnected from the device at a later time to allow for device replacement, usually due to battery depletion of the generator. This requires the implanted lead connector to be able to be disconnected from the device without the connector becoming damaged. This is critical since implanted leads are nearly always left in place and intended to be re-used with the new, replacement device.

Implantable leads and their lead connectors are typically designed to be very flexible and are assembled using adhesive bonds, crimps and welds that form joints in the lead connector. As a result, the lead connector joints and materials are able to withstand only very limited applied disconnection and lead connector withdrawal forces. However, the lead connector joints and the lead connector materials are often exposed to much greater forces during the disconnection. Much higher removal forces are often required because of swelling in the materials on the lead connector interface with the device connector cavity securing mechanisms after several years of implant. This can cause the lead connector to stick inside the cavity. Thus, the much higher withdrawal forces are often necessary to remove the lead connector from the device connector cavity. Such forces can severely damage the lead connector and then render the lead connector to be dysfunctional. Moreover, it can be very difficult or even impossible for the physician to be able to discern whether the lead connector has been damaged. Thus, a damaged lead connector can often become re-used with a new device without it being known that the connector is damaged. This can result in significant clinical problems.

SUMMARY OF THE INVENTION

The present invention overcomes the problems and disadvantages of prior art lead connectors by providing strain relief within a lead connector to protect the lead connector from damage during its disconnection from an associated device.

In accordance with the broader aspects of the present invention, the strain relief is provided by a strain relief member which is connected between a connector terminal and a conductor of the lead that couples a lead electrode to the connector terminal.

In accordance with the present invention, the lead is elongated and has a distal end, a proximal end, an electrode, and a conductor coupled to the electrode and extending to the proximal end of the lead. A connector on the lead proximal end connects the conductor to a mating implantable device connector. The lead connector includes a terminal coupled to the conductor and a string relief member connected between the conductor and the terminal.

In accordance with a particular aspect of the present invention, the connector further includes an anchor longitudinally fixed on the lead proximal to the terminal. The strain relief member is connected between the anchor and the connector terminal.

The lead connector includes a body and the anchor is preferably affixed on the lead conductor within the connector body.

The strain relief member is preferably formed of a flexible, non-stretchable material, such as a flexible, non-stretchable cable fabricated with a suitable metal alloy material. The strain relief member may more preferably be formed of a nickel metal alloy, such as MP-35N.

The connector terminal preferably includes a pin terminal having a crimp sleeve secured to the conductor. The relief member then preferably extends between the anchor and the crimp sleeve.

The present invention still further provides a method of providing an implantable cardiac lead with a connector having strain relief wherein the lead is elongated and has a distal end, a proximal end, an electrode at the distal end, and a conductor coupled to the electrode and extending to the proximal end. The method includes the steps of securing a connector body to the proximal end of the lead, providing the connector body with a terminal, affixing an anchor within the lead body distal to the terminal, coupling the terminal to the lead conductor, and connecting a strain relief member between the anchor and the terminal.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

Figure 1:
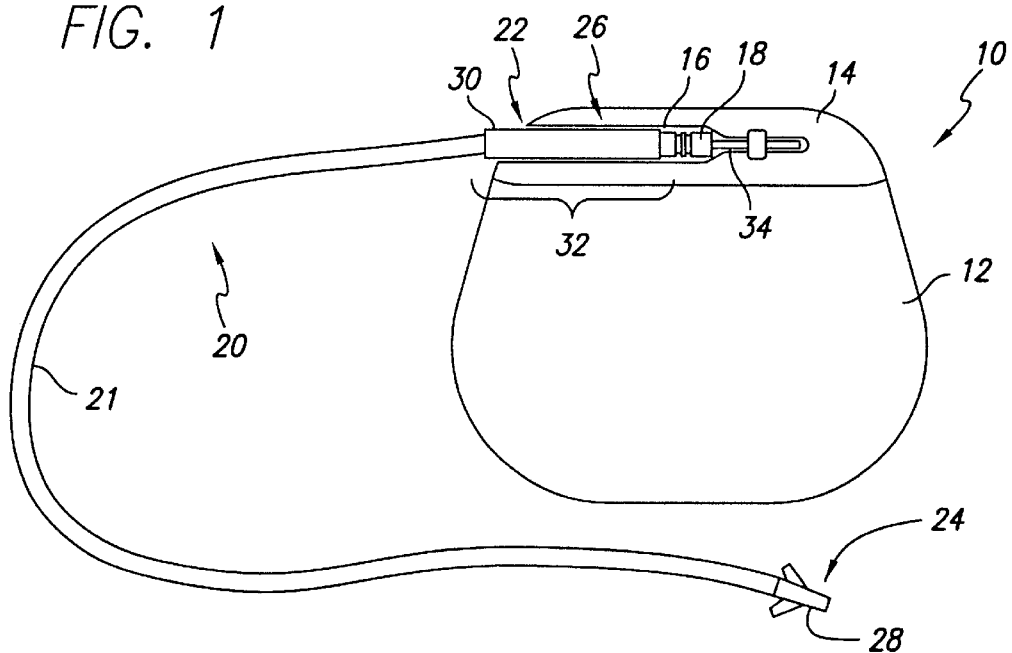
FIG. 1 is a plan view with portions cut away illustrating an implantable cardiac lead embodying the present invention connected to an associated implantable cardiac stimulation device.

The following description is of the best mode presently contemplated for practicing the present invention. This description is not to be taken in a limiting sense but is made merely for the purpose of describing the general principles of the invention. The scope of the invention should be ascertained with reference to the issued claims. In the description of the invention that follows, like reference numerals or reference designators will be used to refer to like parts or elements throughout.

Referring now to FIG. 1, it shows an implantable cardiac lead 20 embodying the present invention. The lead 20 is connected to an associated implantable cardiac stimulation device 10.

The device 10 includes a conductive housing 12, often referred to as the "can", "case" or "case electrode" which may be programmably selected to act as a return electrode for "unipolar" pacing/sensing modalities. Although defibrillation electrodes are not illustrated in FIG. 1, those skilled in the art would appreciate that the housing 12 may further be used as a return electrode alone or in combination with one or more defibrillation electrodes for providing defibrillation therapy. Hence, it is to be understood, that the present invention may be practiced with any form of cardiac stimulation device which includes at least one implantable cardiac lead, whether that device be a pacemaker, a defibrillation, or a device which combines pacing and defibrillation therapy. The device 10 further includes an insulated header assembly 14. As is well known in the art, the insulated header assembly 14 includes a connector cavity 16 configured to receive a mating lead connector 22 of the lead 20 to be described hereinafter. The device connector cavity 16 employs therein a device connector 18 for electrically coupling the device 10 to the lead 20.

The lead 20 as illustrated in FIG. 1 includes an elongated lead body 21 having a distal end 24 and a proximal end 26. The lead distal end 24 includes a sensing/pacing electrode 28 which may be positioned in a patient's heart to make electrical connection to a desired chamber of the heart. Although only one electrode is illustrated in FIG. 1, it will be understood by those skilled in the art that the lead 20 may include a plurality of electrodes. Still further, those electrodes may be pacing electrodes, sensing electrodes, defibrillation electrodes, or a combination of pacing, sensing and defibrillation electrodes. Embodiments of the present invention may be employed to advantage in all such forms of leads.

The proximal end 26 of the lead 20 includes the lead connector 22 embodying the present invention. The connector 22 has a body 30 formed in part by a grip zone 32 which may be gripped for removal of the connector 22 from the device connector cavity 16. The lead terminates in a pin terminal 34 which extends proximally from the connector body 30 and is configured to mate with the device connector 18. A conductor 36 (FIG. 2) extends proximally from the electrode 28 to the proximal end 26 of the lead 20 to couple the pin terminal 34 to the electrode 28. The conductor 36, as is common practice, is preferably formed of MP-35N, a nickel, cobalt, molybdenum alloy coil wire. This imparts flexibility to the conductor 36. It also renders the coil conductor fragile and vulnerable to damage by longitudinal forces imparted to the connector 22 during removal of the connector from the device 10. More specifically, when the connector 22 is removed, the connector is gripped in the grip zone 32. A removal force is then imparted to the connector 22 in a distal direction to the device 10. As previously described, such removal forces may necessarily be excessive for removal and may be sufficient to cause damage to prior art lead connectors. Such damage, however, is precluded by virtue of the present invention as may be seen from the preferred embodiment thereof illustrated in FIG. 2.

Figure 2:
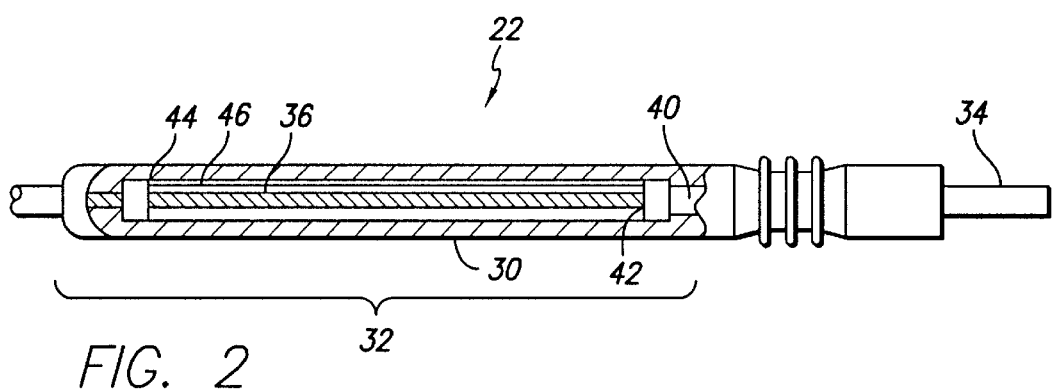
FIG. 2 is a side plan view, partly in cross section, illustrating a cardiac lead connector configured in accordance with a preferred embodiment of the present invention.

FIG. 2 shows the connector 22 in greater detail. The grip zone 32 of the connector body 30 is formed from a suitable material, such as silicone rubber, for example. The conductor 36 extends through the body 30 to a crimp sleeve 40. The crimp sleeve is formed of a rigid conductive material and secures the conductor 36 to the pin terminal 34. The crimp sleeve includes an annular shoulder 42.

Secured to the conductor 36, as by soldering, crimping, or welding, is an anchor 44. The anchor is embedded within the body 30 distal to the terminal pin 34. A strain relief member 46 extends between the anchor 44 and the shoulder 42 of the crimp sleeve 40. The strain relief member 46 more particularly extends adjacent to the conductor 36 and within the body 30 of the connector 22. The strain relief member 46 is elongated and preferably formed of a flexible, non-stretchable material such as a flexible, non-stretchable cable formed from a suitable, strong material such as a nickel alloy. One such nickel alloy is commonly known in the art as MP-35N, a nickel, cobalt, molybdenum metal alloy.

When the connector is to be removed from the device connector cavity 16, the connector 22 is gripped in the grip zone 32. A longitudinal removal force is then applied to the connector 22 for its removal. The strain relief member 46, not withstanding the removal forces, precludes extension of and potential damage to the conductor 36. This provides strain relief for the conductor 36 and the joints of the connector 22. In this manner, the connector is protected from damage which otherwise may result as a consequence of the removal forces.

Figure 3:
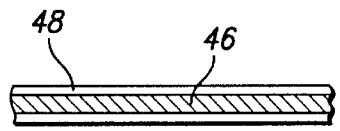
FIG. 3 is a partially cross-sectional view of a strain relief member covered by an insulator in accordance with further aspects of the invention.

FIG. 3 shows the strain relief member 46 covered by an insulator coating 48. The insulator 48 may be polyurethane, silicone rubber, ETFE (ethylenetetrafluoroethylene) or PTFE (polytetrafluoroethylene), for example, and serves to protect the strain relief member and to preclude it from electrically contacting any lead components other than those to which it is secured.

While the invention has been described by means of specific embodiments and applications thereof, it is understood that numerous modifications and variations could be made thereto by those skilled in the art without departing from the spirit and scope of the invention. For example, the strain relief member may be connected to the pin end of the terminal at one end and to a non-conductive lead body component at the other end. It is therefore to be understood that within the scope of the claims, the invention may be practiced otherwise than as specifically described herein.

What is claimed is:

1. A method of providing an implantable cardiac lead with a connector having strain relief, the lead being elongated and having a distal end, a proximal end, an electrode at the distal end, and a conductor coupled to the electrode and extending to the proximal end, the method including the steps of:

securing a connector body to the proximal end of the lead;

providing the connector body with a terminal;

affixing an anchor within the connector body distal to the terminal;

coupling the terminal to the conductor; and connecting a strain relief member between the anchor and the terminal;

wherein the affixing step includes the step of affixing the anchor to the conductor.

2. The method of claim 1 including the further step of forming the strain relief member of a flexible, non-stretchable material.

3. The method of claim 1 including the further step of forming the strain relief member from a flexible, non-stretchable cable.

4. The method of claim 1 including the further step of forming the strain relief member of a metal alloy.

5. The method of claim 4 wherein the metal alloy is a nickel alloy.

6. The method of claim 5 wherein the metal alloy is MP-35N.

7. The method of claim 4 including the further step of covering the strain relief member with an insulator.

8. The method of claim 1 wherein the affixing step includes the step of affixing the anchor within the connector body.

9. The method of claim 1 wherein the step of connecting the strain relief member to the terminal includes the step of extending the strain relief member from the anchor to the terminal adjacent the conductor.

10. The method of claim 1 including the further step of providing the terminal with a crimp sleeve, wherein the coupling step includes the step of coupling the conductor to the crimp sleeve, and wherein the connecting step includes extending the strain relief member from the anchor to the crimp sleeve.

11. In an implantable cardiac lead, the lead having an elongated body, a distal end, a proximal end, an electrode, and a conductor coupled to the electrode and extending to the lead proximal end, a connector for connecting the conductor to a mating implantable device connector and comprising:

terminal means coupled to the conductor for selectively coupling the conductor to the mating connector; and strain relief means for providing strain relief between the conductor and the terminal means upon removal of the lead connector from the device connector;

wherein the strain relief means includes anchor means for providing a secure connection between the conductor and the strain relief means.

12. The cardiac lead of claim 11 wherein the strain relief means is formed of a flexible, non-stretchable material.

13. The cardiac lead of claim 11 wherein the strain relief means is a flexible, non-stretchable cable.

14. The cardiac lead of claim 11 wherein the strain relief means is formed of a metal alloy.

15. The cardiac lead of claim 14 wherein the metal alloy is a nickel alloy.

16. The cardiac lead of claim 15 wherein the nickel alloy is MP-35N.

17. The cardiac lead of claim 14 further including an insulator covering the strain relief means.

18. The cardiac lead of claim 11 wherein the strain relief means is elongated and extends distally from the anchor means to the terminal means adjacent to the conductor.

19. The cardiac lead of claim 11 wherein the anchor means is fixed on the conductor.

20. The cardiac lead of claim 11 wherein the terminal means includes a pin terminal having a crimp sleeve for securing the conductor to the terminal means.

21. The cardiac lead of claim 20 wherein the strain relief means is elongated and extends from the anchor to the crimp terminal.

22. In an implantable cardiac lead, the lead being elongated and having a distal end, a proximal end, an electrode, and a conductor coupled to the electrode and extending to the lead proximal end, a connector on the lead proximal end configured to connect the conductor to a mating implantable device connector and comprising:

a body;

a terminal carried by the body and coupled to the conductor;

an anchor fixed in the body distal to the terminal; and a strain relief member connected between the anchor and the terminal;

wherein the anchor is fixed on the conductor.

23. The cardiac lead of claim 22 wherein the strain relief member is formed of a flexible, non-stretchable material.

24. The cardiac lead of claim 22 wherein the strain relief member is a flexible, non-stretchable cable.

25. The cardiac lead of claim 22 wherein the strain relief member is formed of a metal alloy.

26. The cardiac lead of claim 25 wherein the metal alloy is a nickel alloy.

27. The cardiac lead of claim 26 wherein the nickel alloy is MP-35N.

28. The cardiac lead of claim 25 further including an insulator covering the strain relief member.

29. The cardiac lead of claim 22 wherein the strain relief member is elongated and extends from the anchor to the terminal adjacent the conductor.

30. The cardiac lead of claim 22 wherein the terminal includes a pin terminal having a crimp sleeve secured to the conductor.

31. The cardiac lead of claim 30 wherein the strain relief member is elongated and extends from the anchor to the crimp sleeve.

* * * * *